United States Patent [19]

Bouraly et al.

[11] Patent Number: 5,437,676
[45] Date of Patent: Aug. 1, 1995

[54] KNEECAP CUTTING DEVICE FOR THE FITTING OF A TOTAL KNEE REPLACEMENT

[75] Inventors: Jean-Pierre Bouraly, Montbeliard; Jurg Aebi, Rodez; Philippe Beaufils, Magny les Hameaux; Michel de Lestang, Amiens; Jean-Gilles Gaffuri, Rumilly rn Cambresis; Hervé Hourlier, Wignehies; Jean-Jacques Lallement, St Andre les Vergers; Philippe Legroux, Le Bouscat; Jean-Paul Levai, Clermond-Ferrand; Gérald Pondaven, Quimper; Pierre Schuster, Saint Avold; Christian Vergnat, Metz, all of France

[73] Assignees: Developpement d'Implants Orthopediques et Medicaux; Protek Synthes, both of Etupes Cedex, France

[21] Appl. No.: 187,287
[22] Filed: Jan. 27, 1994
[51] Int. Cl.6 ............................................. A61B 17/56
[52] U.S. Cl. .................................... 606/88; 606/87
[58] Field of Search ..................... 606/88, 87, 86, 82, 606/79, 80, 83, 84, 85; 623/20, 18

[56] References Cited

U.S. PATENT DOCUMENTS

| | | | |
|---|---|---|---|
| 4,565,192 | 1/1986 | Shapiro | 606/88 |
| 4,633,862 | 1/1987 | Petersen | 606/88 |
| 4,706,660 | 11/1987 | Petersen | 606/86 |
| 4,952,213 | 8/1990 | Bowman et al. | |
| 5,021,055 | 6/1991 | Burkinshaw et al. | 606/82 |
| 5,108,401 | 4/1992 | Insall et al. | |
| 5,129,907 | 7/1992 | Heldreth et al. | 606/80 |
| 5,129,908 | 7/1992 | Petersen | 606/88 |
| 5,147,365 | 9/1992 | Whitlock et al. | 606/88 |
| 5,284,482 | 2/1994 | Mikhail | 606/88 |
| 5,342,364 | 8/1994 | Mikhail | 606/79 |

FOREIGN PATENT DOCUMENTS

| | | | |
|---|---|---|---|
| 0466659 | 1/1992 | European Pat. Off. | |
| 925329 | 5/1982 | U.S.S.R. | 606/88 |
| WO91/04715 | 4/1991 | WIPO | |

Primary Examiner—Stephen C. Pellegrino
Assistant Examiner—Guy Tucker
Attorney, Agent, or Firm—Pollock, Vande Sande & Priddy

[57] ABSTRACT

A kneecap cutting guide device for the fitting of a total knee replacement includes, a trial femur component having an artificial trochlea, a side hole made on at least one edge of said trial femur component, and a central hole made in the center of said trochelea. An ancillary device includes a fastening dog-point designed to cooperate with the side hole of the trial femur component. A kneecap plate is designed to be placed in a position of resting on the kneecap and a mechanism to center the plate in relation to said central hole of the artificial trochlea is provided. The guide device further incorporates means to shift the kneecap plate, enabling a crosswise motion with respect to said trochlea and an axial motion parallel to the central hole. There is also a mechanism for locking the plate in position and a surface for guiding a blade to cut the kneecap parallel to the plane of the trochlea.

7 Claims, 3 Drawing Sheets

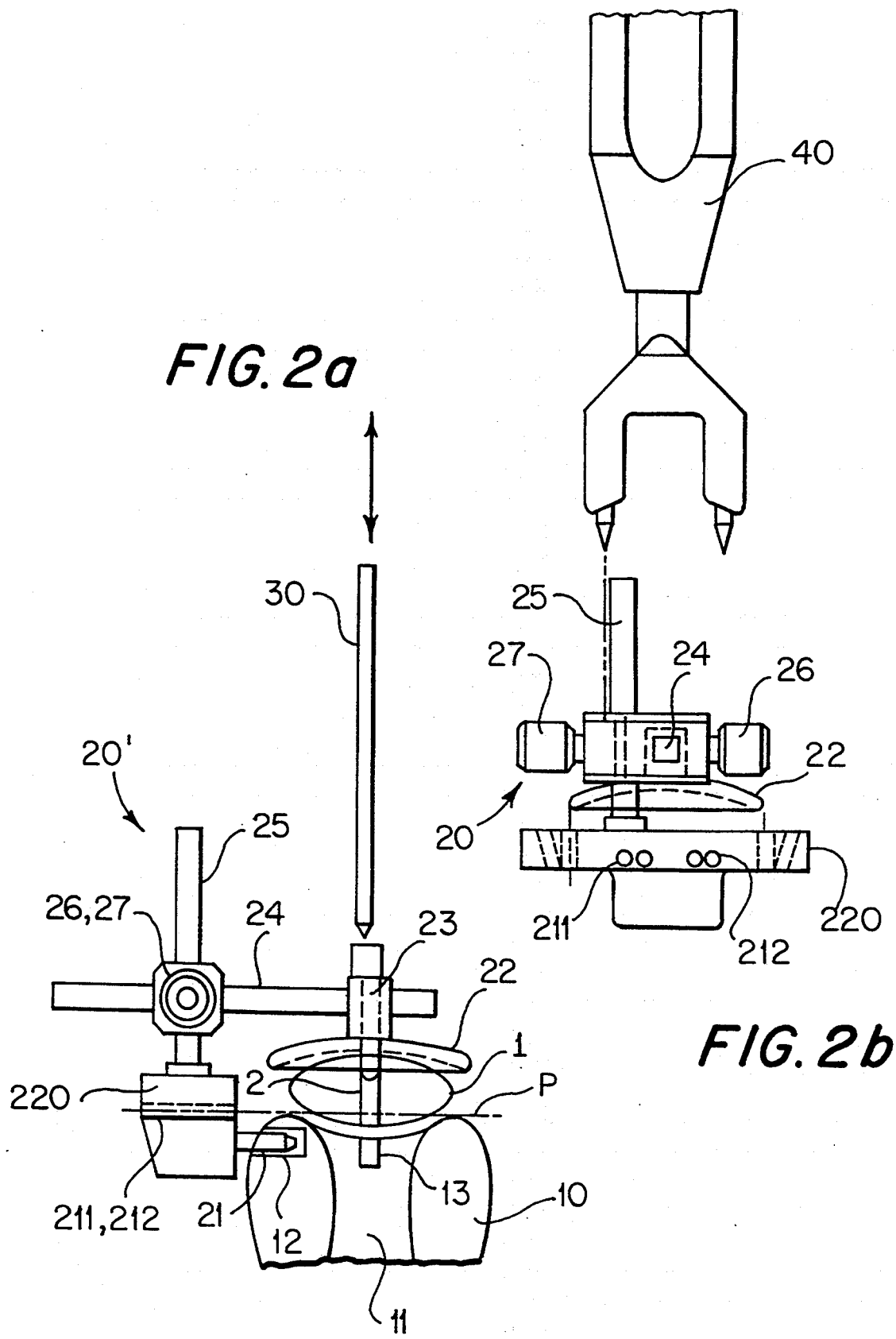

KNEECAP CUTTING DEVICE FOR THE FITTING OF A TOTAL KNEE REPLACEMENT

BACKGROUND OF THE INVENTION

1. FIELD OF THE INVENTION

The present invention relates to a kneecap or patella cutting device for the fitting of a total knee replacement or prosthesis.

The invention can be applied in an especially advantageous way in the field of bone resurfacing prosthesis relating to the knee joint.

Three-compartmental total knee replacements are constituted by a tibia part, a kneecap part and a femur part that has notably an artificial trochlea. In this type of prosthesis, the kneecap is designed to move in said artificial trochlea through said kneecap component.

2. DESCRIPTION OF THE PRIOR ART

Usually, in a total knee replacement operation, the anatomical kneecap is cut and then drilled through with locking holes for the implanting of the future kneecap component designed to cooperate with the artificial trochlea that is prepared in the femur component.

At present, kneecap cutting is always done separately from the femur and without any reference other than an anatomical one.

The result thereof is that, in certain cases, since the cutting is not parallel to the plane of the trochlea, the kneecap component is badly positioned. The kneecap is then unstable, and therefore often tends to get dislocated, i.e. to get out of the groove formed by the trochlea of the femur component. To put it briefly, the action of the kneecap during the bending and stretching of the knee may be likened to that of a pulley that compensates for the tendency of the femur/tibia joint to get dislocated. To the extent that the equivalent of the pulley is positioned crosswise, it tends to protrude and consequently to come out of the housing into which it is fitted.

For example, we may cite a cutting method in which the kneecap is firstly put out of joint and then held by forceps wherein it is cut or milled. However, this type of technique cannot be used to obtain a cutting of the kneecap that is perfectly parallel to the plane of trochlea of the femur component.

Hence, the technical problem to be resolved by the object of the present invention is that of proposing a kneecap cutting device, for the fitting of a total knee replacement, by which it is possible to obtain cutting that is systematically parallel to the plane of the trochlea.

SUMMARY OF THE INVENTION

The solution provided by the present invention to the technical problem raised is one wherein said device comprises, firstly, a trial femur component having an artificial trochlea, at least one side hole made on at least one edge of said trial femur component and a central hole made in the center of said trochlea and, secondly, an ancillary device comprising a fastening dog-point designed to cooperate with said side hole of the trial femur component, a kneecap plate designed to be placed in a position of resting on the kneecap, a means to center said plate in relation to said central hole of the artificial trochlea, means to shift the kneecap plate enabling a crosswise motion with respect to said trochlea and an axial motion parallel to the central hole, means for the locking of said plate in position and means to cut the kneecap in parallel to the plane of said trochlea.

The device according to the invention therefore makes it possible, by means of fixed references taken with respect to the trial femur component itself, to obtain a cutting of the kneecap that is perfectly parallel to the plane of the artificial trochlea.

A first embodiment of the device according to the invention is designed so that said cutting means are constituted by a lateral slot, parallel to the plane of the artificial trochlea, that is made in a first template positioned on the ancillary device and that has an oscillating saw inserted into it. This embodiment, which enables the kneecap cutting operation with the kneecap in position, nevertheless has the drawback wherein the surgeon cannot have an exact view of how the cutting is really being done.

This is why the invention provides for a second embodiment of the kneecap cutting device that gives the practitioner the possibility of monitoring the cutting of the kneecap when it is carried out. In this second embodiment, said cutting means are constituted by a cutting guide that is fitted to two pins going through the kneecap and is positioned in parallel to the plane of the artificial trochlea from two through-holes made in a second template positioned on the ancillary device.

BRIEF DESCRIPTION OF THE DRAWINGS

The following description, made with reference to the appended drawings which are given by way of non-restrictive examples, will give a clear understanding of the content of the invention and the way in which it can be achieved.

FIG. 1a shows a front view of a first device for the cutting of a kneecap in accordance with the invention;

FIG. 1b shows a side view corresponding to the front view of FIG. 1a;

FIG. 2a shows a front view of a second device for the cutting of a kneecap in accordance with the invention;

FIG. 2b shows a side view corresponding to the front view of FIG. 2a.

FIG. 3b shows a front view corresponding to the side view of FIG. 3a.

MORE DETAILED DESCRIPTION

Figures 1A, 1B:
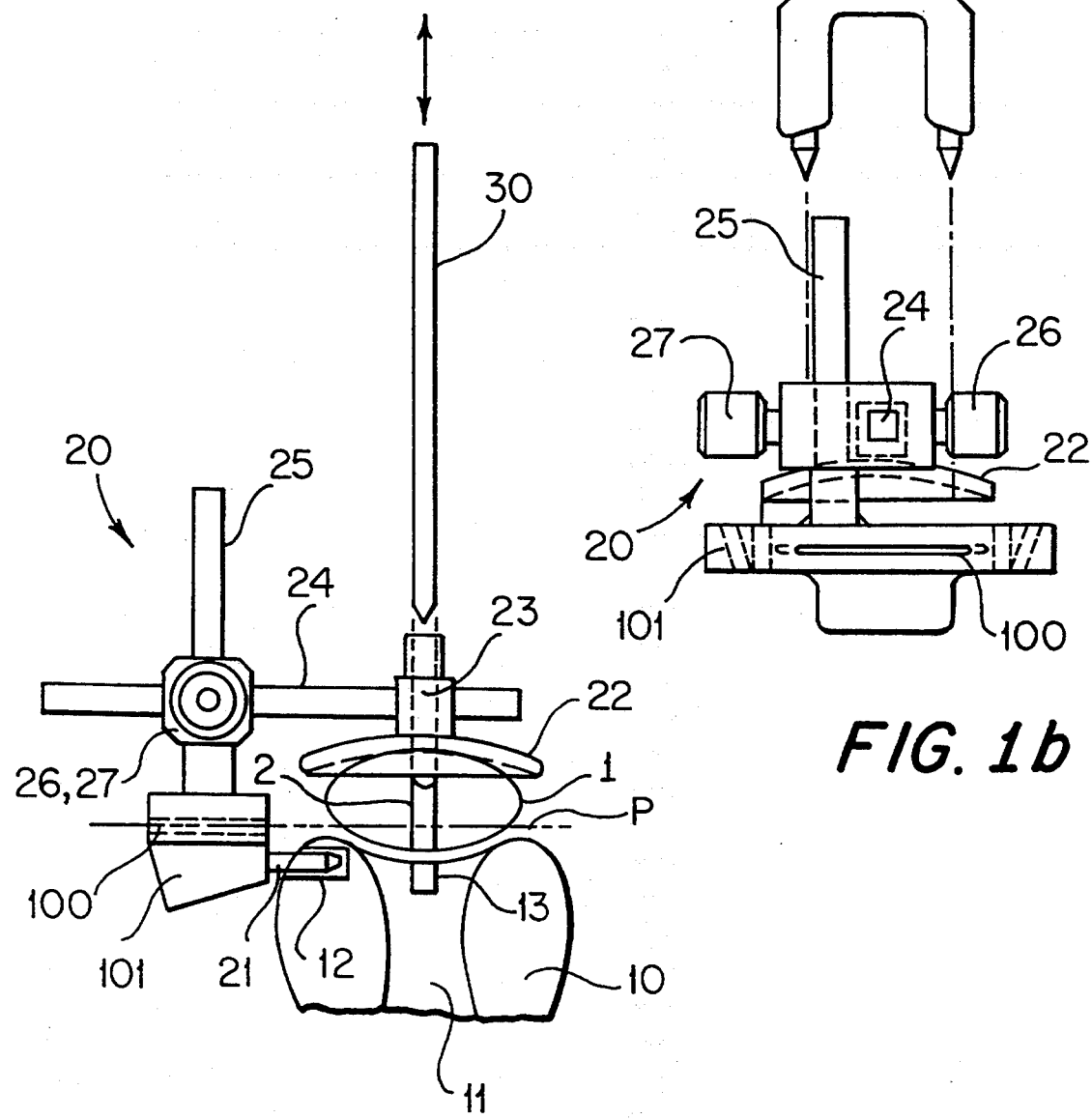

FIGS. 1a and 1b show front and side views of a first device for the fitting of a total knee replacement comprising, firstly, a trial femur component 10 having an artificial trochlea 11, at least one side hole 12 made on at least one edge of said trial femur component, and a central hole 13 made in the center of said trochlea. Secondly, the kneecap cutting device shown in FIGS. 1a and 1b also comprises an ancillary device 20 with a fastening dog-point 21 designed to cooperate with the side hole 12 of the trial femur component 10, so as to fix the ancillary device to said femur component throughout the operation. In a practical way, there is provision for two fastening dog-points and two corresponding side holes on each edge of the trial femur further comprises a dome-shaped kneecap plate 22 designed to be positioned so that it rests against the kneecap 1.

The kneecap plate 22 is provided with a means for centering in relation to the central hole 13 of the artificial trochlea. This centering means is constituted by a centering hole 23 made in the center of the plate and designed to be brought into a position of coincidence with said central hole 13 by means of an alignment pin 30 and by the application of a motion parallel to the trochlea 11, this motion being permitted by means for shifting the plate 22. In the embodiment shown in FIGS. 1a and 1b, said shifting means are constituted by a transversal rod 24 supporting said kneecap plate, sliding with said transversal motion, and by an axial rod 25 along which there slides said transversal rod in an axial shifting motion that is parallel to the central hole 13 of the artificial trochlea 11.

FIGS. 1a and 1b also show the presence, on the ancillary device 20, of means to lock the kneecap plate 22 in position, said means being formed by a first screw knob 26 to lock the plate to the transversal rod 24 and a second screw knob 27 to lock the transversal rod to the axial rod 25.

Finally, the kneecap cutting ancillary device of FIGS. 1a and 1b comprises means for cutting the kneecap 1 in a direction parallel with the plane P of the artificial trochlea 11 constituted, in this example, by a lateral slot 100 parallel to the plane P of the trochlea, made in a first template 101 positioned on the ancillary device 20, an oscillating saw (not shown in FIGS. 1a and 1b) being introduced into this slot 100.

The kneecap cutting method that implements the device illustrated in FIGS. 1a and 1b then comprises the following operations:

dislocating the kneecap 1;
positioning the trial femur component 10;
fixing the ancillary kneecap cutting device 20 to said trial femur element by cooperation between the fixing dog-points 21 and the side holes 12;
by implementation of the transversal movement of said shifting means 24, 25, bringing the centering hole 23 of the kneecap plate 22 to a position facing the central hole 13 of the trial femur component;
introducing the trial pin 30 through the centering hole 23 up to the central hole 13;
locking the kneecap plate 22 in a centered position with respect to the trochlea 11 by means of the locking screw knobs 26, 27;
removing the alignment pin 30;
releasing the plate 22 by applying the axial motion of the shifting means 24, 25;
reducing the kneecap 1 and placing it directly on the trial femur component 10;
applying the kneecap plate 22 against the kneecap so as to center it with respect to the trochlea 11;
drilling the kneepcap 1 with an axial through-hole 2 by using a drilling means fitted into the centering hole 23 of the kneecap plate;
introducing, through the centering hole, a stop pin into said axial through-hole 2;
cutting the kneecap by means of the oscillating saw through the lateral slot 100.

During the cutting operation, the kneecap 1 may be held firmly in position by means of a supporting sleeve 40 applied to the kneecap plate 22, as can be seen in FIG. 1b.

FIGS. 2a, 2b, 3a and 3b illustrate a second kneecap cutting device comprising elements common with those of the device shown in FIGS. 1a and 1b. These common elements bear the same reference numbers. The device of FIGS. 2a, 2b, 3a and 3b is distinguished from the previously described device in that the cutting means are constituted by a cutting guide 200 fitted to two pins 201, 202 going through the kneecap 1 and positioned in parallel to the plane of the artificial trochlea 11 from two through-holes 211, 212 made in a second template 220 positioned on the ancillary element 20'.

FIG. 1b shows two sets of through-holes. The practitioner can choose between these sets of holes according to the size of the anatomical kneecap considered.

Figure 3A:
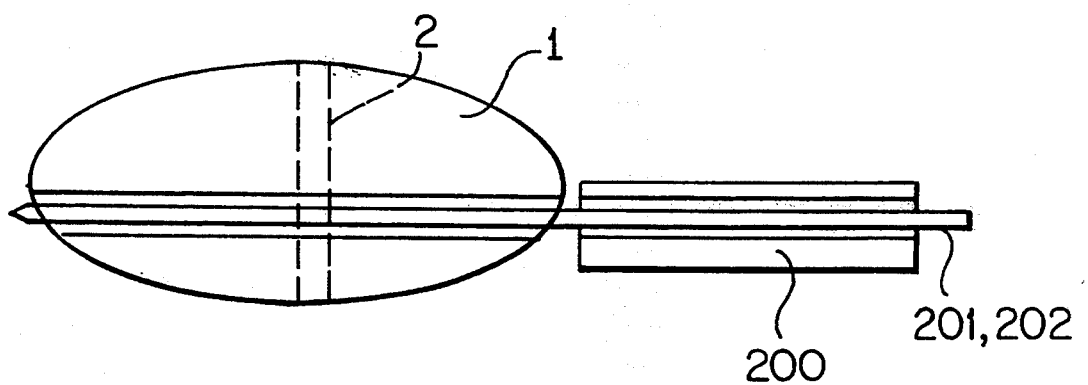
FIG. 3a shows a side view of a kneecap provided with a cutting guide.
Figure 3B:
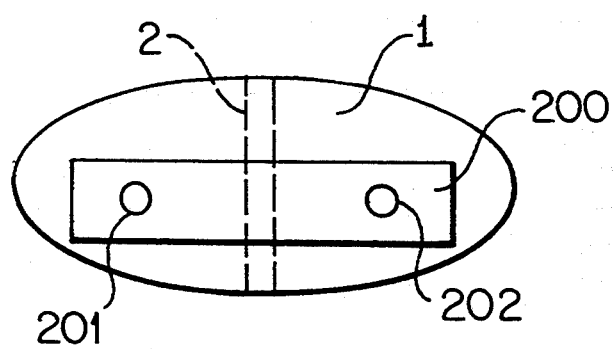

Similary, FIGS. 3a and 3b show that the cutting guide 200 is dissymetrical so as to have two possible cutting levels.

The kneecap cutting method using this second device comprises the same first steps as the method implementing the first cutting device until the step for the introduction of the stop pin into the axial through-hole 2, this step being then followed by the operations of:

drilling the kneecap 1 with two transversal through-holes parallel to the plane P of the trochlea 11 by means of the drilling template 220,
introducing the pins 201, 202 into said transversal through-holes;
again releasing the kneecap plate 22 by the application of the axial motion of said shifting means 24, 25;
dislocating the kneecap 1 fitted with the two pins 201, 202;
fitting the cutting guide 200 to said pins;
cutting the kneecap 1 by means of a saw guided by said cutting guide.

What is claimed is:

1. A kneecap cutting guide apparatus for facilitating the fitting of a total knee replacement, comprising: a trial femur component having
   (a) an artificial trochlea;
   (b) at least one side hole made in an edge of the trial femur component;
   (c) a central hole made in the center of the artificial trochlea; an ancillary device having
   (d) a clamping dog-point for engaging the side hole of the trial femur component;
   (e) a kneecap plate positionable against the kneecap;
   (f) means for centering the plate in fixed relation to the central hole of the artificial trochlea;
   (g) means for shifting the kneecap plate enabling a crosswise motion with respect to the artificial trochlea as well as axial motion parallel to the central hole;
   (h) means for locking the plate in position; and
   (i) means for guiding a bone cutting blade through the kneecap, parallel to a plane of the artificial trochlea.

2. A kneecap cutting guide apparatus as set forth in claim 1, wherein the blade guiding means further comprises a lateral slot/brimmed in a template portion of the ancillary device, the slot oriented parallel to the plane of the artificial trochlea.

3. A kneecap cutting guide apparatus as set forth in claim 1, wherein the blade guiding means further comprises:
   a guide member having pins extending through holes in the member, the pins adapted to be pass through respective holes in a template portion of the ancillary device, for receipt within corresponding holes in the kneecap, the pins positioned parallel to the plane of the artificial trochlea: and
   a surface for guiding a blade during cutting.

4. A kneecap cutting guide apparatus as set forth in claim 3, wherein the guide member has oppositely situated surfaces for selectively guiding a blade during cutting;

the surfaces of the guide member being non-symmetrically oriented in relation to the holes extending therethrough, thereby enabling the surfaces to be selectively employed at respectively different cutting levels in relation to the plane of the artificial trochlea.

5. A kneecap cutting guide apparatus as set forth in claim 1, wherein the centering means is a centering hole made in the center of the kneecap plate and positioned coaxial to the central hole in the artificial trochlea.

6. A kneecap cutting guide apparatus as set forth in claim 1, wherein the shifting means further comprises:

a transversal rod slidably supporting the kneecap plate; and an axial rod connected with the transversal rod, and positioned in parallel spaced relation to the central hole in the artificial trochlea, for varying the axial position of the kneecap plate.

7. A kneecap cutting guide apparatus as set forth in claim 6, wherein the locking means further comprises:

a first screw knob for locking the kneecap plate to the transversal rod; and a second screw knob for locking the transversal rod to the axial rod.

* * * * *